(12) United States Patent
Ishihara

(10) Patent No.: US 9,901,253 B2
(45) Date of Patent: Feb. 27, 2018

(54) FLUORESCENCE OBSERVATION APPARATUS

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 12 days.

(21) Appl. No.: 15/163,739

(22) Filed: May 25, 2016

(65) Prior Publication Data

US 2016/0262622 A1 Sep. 15, 2016

Related U.S. Application Data

(63) Continuation of application No. PCT/JP2014/081427, filed on Nov. 27, 2014.

(30) Foreign Application Priority Data

Nov. 28, 2013 (JP) .................................. 2013-246521

(51) Int. Cl.
*A61B 5/00* (2006.01)
*A61B 1/06* (2006.01)
*A61B 1/04* (2006.01)

(52) U.S. Cl.
CPC .............. *A61B 5/0071* (2013.01); *A61B 1/04* (2013.01); *A61B 1/043* (2013.01); *A61B 1/0638* (2013.01);
(Continued)

(58) Field of Classification Search
CPC ..... A61B 1/043; A61B 1/0646; A61B 1/0638; A61B 5/0071
See application file for complete search history.

(56) References Cited

U.S. PATENT DOCUMENTS 6,293,911 B1 9/2001 Imaizumi et al.
7,179,222 B2 2/2007 Imaizumi et al.
(Continued)

FOREIGN PATENT DOCUMENTS

EP 1964503 A1 9/2008
JP 2007-090044 A 4/2007
(Continued)

OTHER PUBLICATIONS

International Search Report dated Mar. 3, 2015 issued in PCT/JP2014/081427.
(Continued)

*Primary Examiner* — Michael D Abreu
(74) *Attorney, Agent, or Firm* — Scully, Scott, Murphy & Presser, P.C.

(57) ABSTRACT

A fluorescence observation apparatus comprising a light source having a single light-emitting portion for emitting white light and excitation light simultaneously and radiates the white light and the excitation light; a light guide that guides the radiated white and excitation lights and simultaneously irradiates the white and excitation lights light onto a specimen; a white-light-image acquisition unit that receives return light of the white light coming from the specimen and acquires a white-light image; a fluorescence-image acquisition unit that receives fluorescence excited in the specimen by the excitation light and acquires a fluorescence image; an illumination-light filter that is disposed between the light-emitting portion and a radiation exit end of the light source, and satisfies the following conditional expression, Pf($\lambda$w)<Pf($\lambda$e), wherein Pf($\lambda$w) and Pf($\lambda$e) are transmittances of the illumination-light filter at a wavelength $\lambda$w in a white-light band and a wavelength $\lambda$e in a excitation-light band.

12 Claims, 9 Drawing Sheets

(52) U.S. Cl.
CPC .......... *A61B 1/0646* (2013.01); *A61B 5/7425* (2013.01); *A61B 2562/0233* (2013.01)

(56) References Cited

U.S. PATENT DOCUMENTS

| | | | |
|---|---|---|---|
| 2007/0046778 A1 | 3/2007 | Ishihara et al. | |
| 2012/0242859 A1* | 9/2012 | Sasaki ................ | A61B 1/00165 348/223.1 |
| 2013/0338439 A1* | 12/2013 | Kosugi .............. | A61B 1/00193 600/111 |

FOREIGN PATENT DOCUMENTS

| | | |
|---|---|---|
| JP | 2007-167325 A | 7/2007 |
| JP | 2011-127933 A | 6/2011 |
| JP | 2012-157383 A | 8/2012 |

OTHER PUBLICATIONS

Chinese Office Action dated Apr. 27, 2017 in Chinese Patent Application No. 201480064088.1.

* cited by examiner

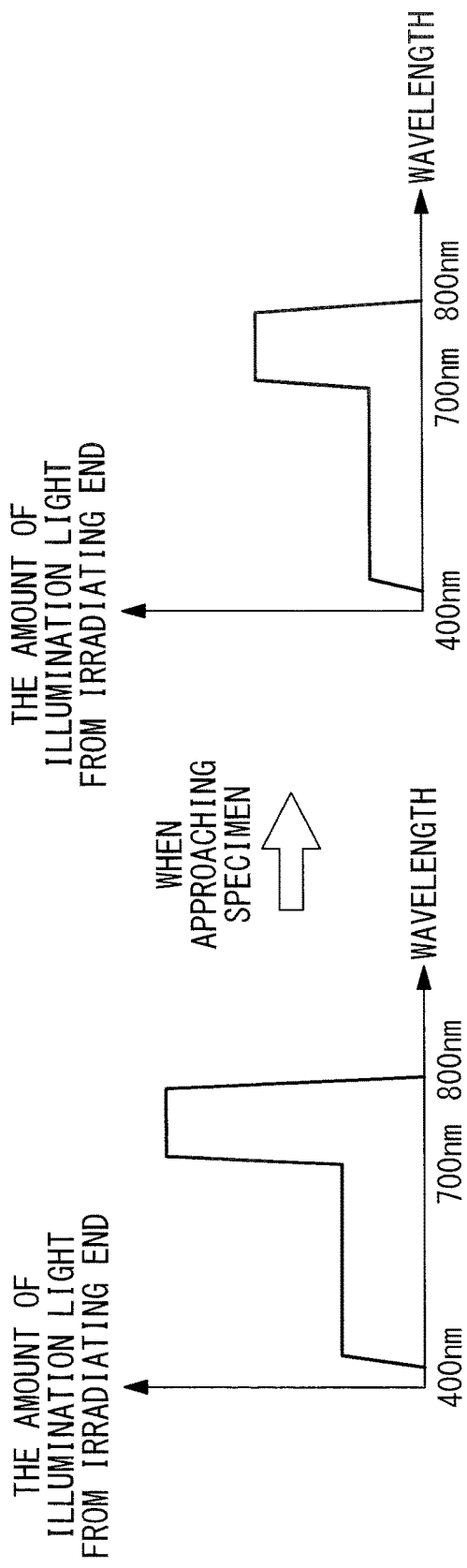

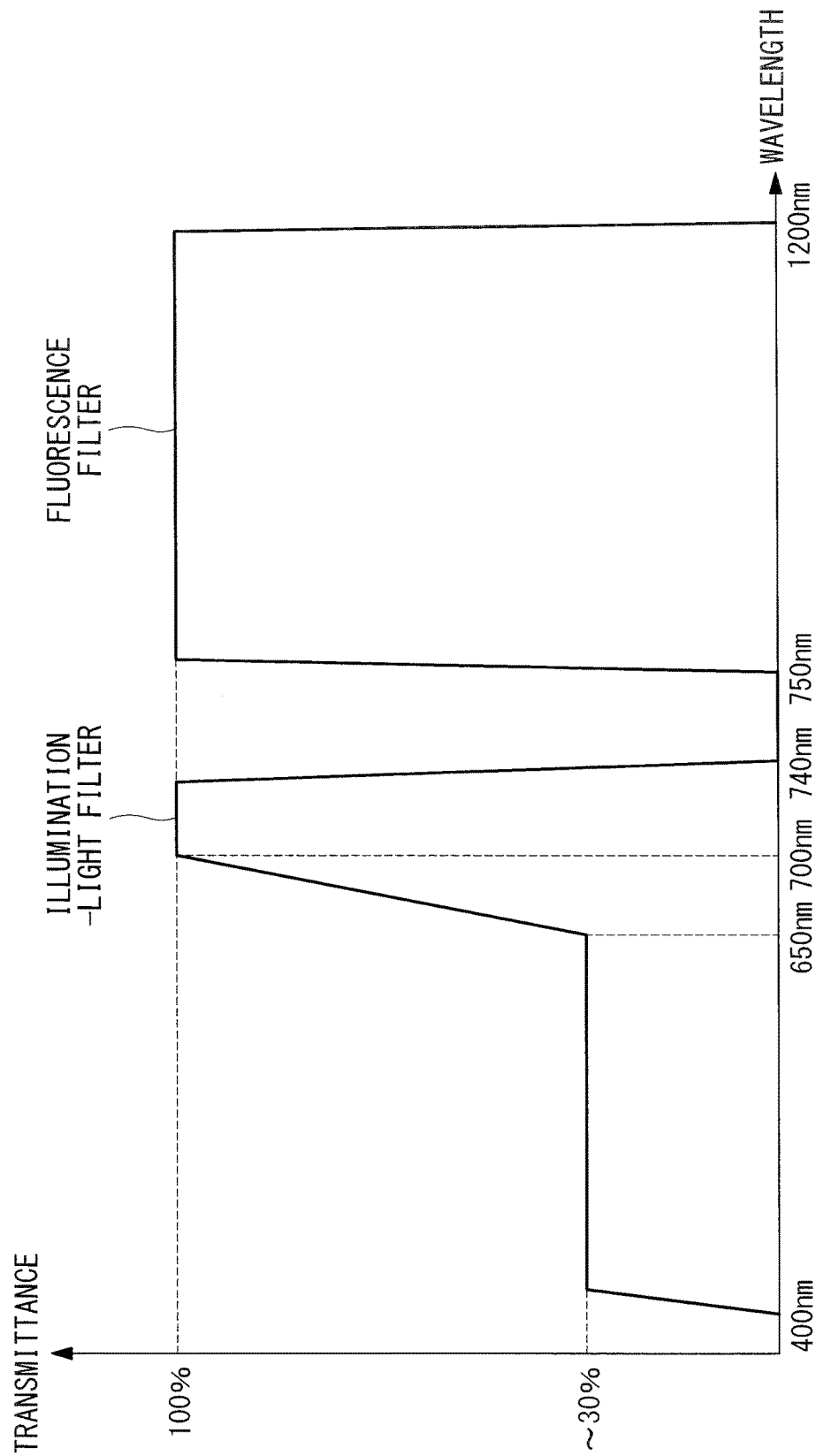

FLUORESCENCE OBSERVATION APPARATUS

CROSS-REFERENCE TO RELATED APPLICATIONS

This application is a Continuation application of International Application No. PCT/JP2014/081427 filed on Nov. 27, 2014, which claims priority to Japanese Application No. 2013-246521 filed on Nov. 28, 2013. The contents of International Application No. PCT/JP2014/081427 and Japanese application No. 2013-246521 are hereby incorporated by reference in its entirety.

TECHNICAL FIELD

The present invention relates to a fluorescence observation apparatus and, in particular, to a fluorescence observation apparatus for observation of a white-light image and a fluorescence image that are generated by receiving return light and fluorescence from a specimen irradiated with white light and excitation light.

BACKGROUND ART

There are conventionally known fluorescence observation apparatuses (for example, PTL 1) in which white light and excitation light in the near-infrared band are simultaneously radiated from the same light source, and a white-light image generated on the basis of return light of the white light coming from a specimen and a fluorescence image generated on the basis of fluorescence produced by the excitation light are observed at the same time.

In general, fluorescence is extremely weak compared with white light. Therefore, in order to simultaneously radiate white light and excitation light from the same light source, as considered in the fluorescence observation apparatus in PTL 1, the amount of white light and the amount of excitation light need to be balanced.

Also, as disclosed in PTL 2, there is a fluorescence observation apparatus in which white light is radiated using a xenon lamp, and excitation light is radiated using a laser.

Further, PTL 3 discloses a configuration in which white light and excitation light are radiated by a frame-sequential method, specifically, by using a time division method.

CITATION LIST

Patent Literature

{PTL 1} Japanese Unexamined Patent Application, Publication No. 2007-90044
{PTL 2} U.S. Pat. No. 7,179,222
{PTL 3} Japanese Unexamined Patent Application, Publication No. 2007-167325

SUMMARY OF INVENTION

An aspect of the present invention provides a fluorescence observation apparatus comprising: a light source unit that has a single light-emitting portion for emitting white light and excitation light simultaneously and that radiates the white light and the excitation light emitted from the light-emitting portion; a light guide part that guides the white light and the excitation light radiated from the light source unit and that simultaneously irradiates the white light and the excitation light onto a specimen; a white-light-image acquisition unit that receives return light of the white light coming from the specimen and that acquires a white-light image; and a fluorescence-image acquisition unit that receives fluorescence excited in the specimen by the excitation light and that acquires a fluorescence image, wherein the light source unit has an illumination-light filter that is disposed between the light-emitting portion and the light guide part, and that satisfies the following conditional expression, $$Pf(\lambda w) < Pf(\lambda e) \tag{1}$$

wherein $Pf(\lambda w)$ is a light transmittance of the illumination-light filter at a wavelength $\lambda w$ in a white-light band, and $Pf(\lambda e)$ is a light transmittance of the illumination-light filter at a wavelength $\lambda e$ in a excitation-light band.

BRIEF DESCRIPTION OF DRAWINGS

FIG. 4B is a graph showing an example of light-amount adjustment control performed in a light-amount adjusting unit applied to the fluorescence observation apparatus according to the second embodiment of the present invention.

FIG. 8 is a graph showing an example of transmittance of an illumination-light filter that has a transmittance which increases stepwisely according to wavelength bands.

DESCRIPTION OF EMBODIMENTS

First Embodiment

A fluorescence observation apparatus according to a first embodiment of the present invention will be described below with reference to the drawings.

Figure 1:
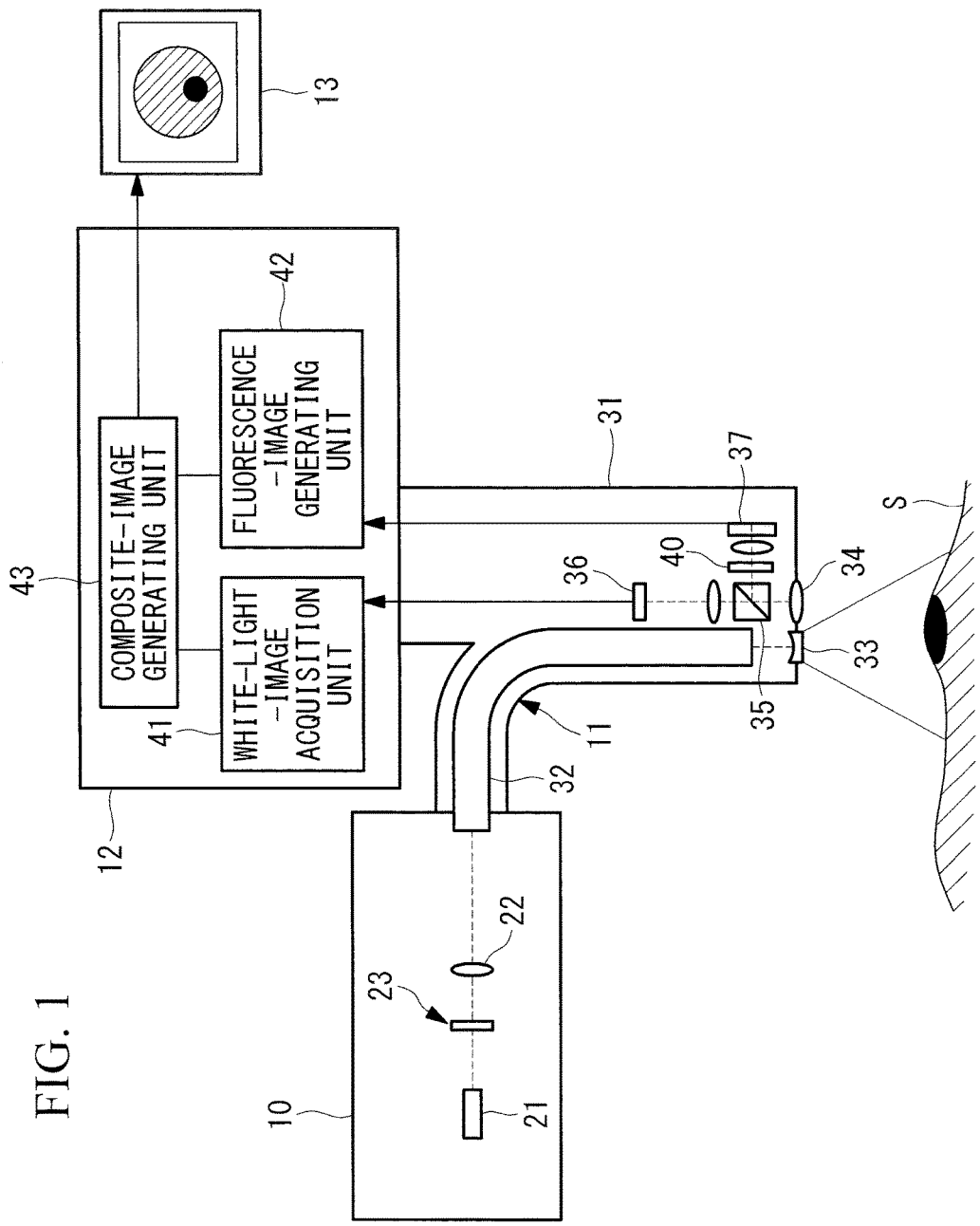
FIG. 1 is a block diagram showing, in outline, a configuration of a fluorescence observation apparatus according to a first embodiment of the present invention.

As shown in FIG. 1, the fluorescence observation apparatus is provided with a light-source device 10 that emits white light and excitation light, an endoscope 11 that is inserted into a body cavity, that guides the white light and the excitation light emitted from the light-source device 10, and that receives light from a specimen S to be examined, an image processing device 12 that generates images on the basis of signals output from the endoscope 11, and a monitor 13 that displays the image generated by the image processing device 12.

The light-source device 10 uses, for example, a xenon lamp 21 as a single light-emitting part for emitting white light and excitation light simultaneously, and the light-source device 10 has an illumination-light filter 23 that transmits light of predetermined wavelengths at a predetermined ratio, among the white light and the excitation light emitted from the xenon lamp 21, and a collimator lens 22 that converts the light that has been transmitted through the illumination-light filter 23 into approximately collimated light. In the light-source device 10, part of the white light and the excitation light emitted from the xenon lamp 21 is transmitted through the illumination-light filter 23, is converted into approximately collimated light by the collimator lens 22, and is emitted toward an entrance end of a light guide fiber 32 which will be described below.

Further, the fluorescence observation apparatus is configured so as to satisfy the following conditional expression.

$$Pf(\lambda w) < Pf(\lambda e) \tag{1}$$

In the expression, $Pf(\lambda w)$ is the light transmittance of the illumination-light filter 23 at a wavelength $\lambda w$ in the white-light band, and $Pf(\lambda e)$ is the light transmittance of the illumination-light filter 23 at a wavelength $\lambda e$ in the excitation-light band.

In other words, the white-light spectrum and the excitation-light spectrum are simultaneously produced in the xenon lamp 21, and the illumination-light filter 23, which is configured such that the transmittance of the excitation light becomes higher than the transmittance of the white light, is used. Accordingly, the intensity of illumination light, per wavelength, to be irradiated onto the specimen can be made higher in the excitation-light band than in the white-light band, and furthermore, white light and excitation light can be irradiated simultaneously. Thus, the following expression is satisfied.

$$W(\lambda w) < E(\lambda e) \tag{1'}$$

In the expression, $W(\lambda w)$ is the intensity of light at the wavelength $\lambda w$ in the white-light band, of illumination light radiated from the endoscope 11, and $E(\lambda e)$ is the intensity of light at the wavelength $\lambda e$ in the excitation-light band, of illumination light radiated from the endoscope 11.

For example, when illumination light having a uniform spectrum in a wavelength band from 400 to 800 nm is emitted, and the amount of light emitted from the xenon lamp is suppressed in order to avoid a situation in which white-light images are too bright, the amount of light in an excitation-light band from 700 to 800 nm is also suppressed, which might make it impossible to obtain a sufficient fluorescence luminance.

Figure 2:
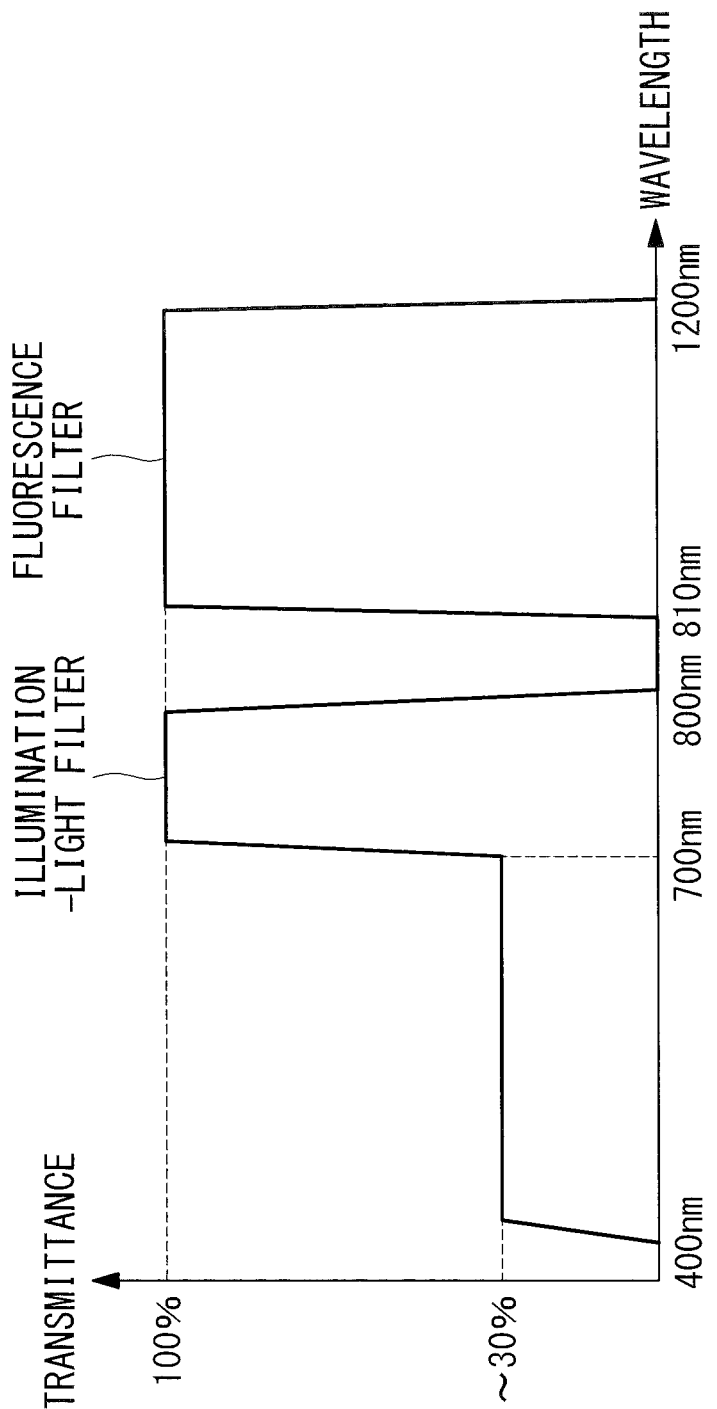
FIG. 2 is a graph showing transmittances of an illumination-light filter and a fluorescence filter applied to the fluorescence observation apparatus according to the first example of the present invention.

As described in this embodiment, the illumination-light filter 23, which suppresses the transmittance in a band from 400 to 700 nm as shown in FIG. 2, is used, thereby avoiding a situation in which white-light images are too bright and thus eliminating the need to suppress the amount of light emitted from the xenon lamp. Therefore, observation can be performed with a sufficient fluorescence luminance, without suppressing the amount of excitation light.

The endoscope 11 has an elongated insertion section 31 to be inserted into the body cavity. The light guide fiber 32 is inserted into the insertion section 31 as a light guide means for guiding white light and excitation light supplied from the light-source device 10 to a distal end thereof and radiating them simultaneously onto the specimen S. Furthermore, an illumination lens 33 is provided at an exit end of the light guide fiber 32, from which white light and excitation light are emitted.

Furthermore, the endoscope 11 is provided with an objective lens 34, a beam splitter 35, a white-light-image acquisition unit 36, and a fluorescence-image acquisition unit 37. The objective lens 34 receives return light coming from the specimen S when white light is radiated from the light guide fiber 32 and via the illumination lens 33, and receives fluorescence produced in the specimen S when excitation light is radiated from the light guide fiber 32 and via the illumination lens 33.

The beam splitter 35 separates the return light and the fluorescence coming from the specimen S so as to make the return light coming from the specimen S, received by the objective lens 34, enter the white-light-image acquisition unit 36 and to make the fluorescence produced in the specimen S, received by the objective lens 34, enter the fluorescence-image acquisition unit 37. The white-light-image acquisition unit 36 receives the return light that is irradiated thereon after being separated by the beam splitter 35 and acquires a white-light image.

The fluorescence-image acquisition unit 37 receives the fluorescence that is irradiated thereon after being separated by the beam splitter 35 and acquires a fluorescence image. Furthermore, a fluorescence filter 40 is provided at a position adjacent to an entrance end of the fluorescence-image acquisition unit 37, so that only fluorescence at predetermined wavelengths is transmitted therethrough (see FIG. 2). Note that an imaging element, for example, a CCD sensor, a monochrome CMOS sensor, or an EM-CCD (Electron Multiplying-CCD) sensor, for fluorescence observation, can be used as the fluorescence-image acquisition unit 37.

The image processing device 12 is provided with a white-light-image generating unit 41 that generates a white-light image on the basis of a signal for the white-light image, sent from the white-light-image acquisition unit 36, a fluorescence-image generating unit 42 that generates a fluorescence image on the basis of a signal for the fluorescence image, sent from the fluorescence-image acquisition unit 37, and a composite-image generating unit 43 that generates a composite image obtained by combining the generated white-light image and fluorescence image. The monitor 13 displays the generated composite image.

The operation of the thus-configured fluorescence observation apparatus will be described below.

An operator inserts the insertion section 31 of the endoscope 11 into the body cavity, guides a distal end portion of the insertion section 31 to a target site, and conduct a fluorescence observation. At this time, prior to the insertion of the insertion section 31 into the body cavity, a fluorescent substance that accumulates at a region after the elapse of a predetermined period of time since administration is administered to the body of the patient in advance. For example, it is possible to use, as a fluorescent substance, a medicinal substance obtained by binding ICG (Indocyanine Green), which is a fluorescent dye, to Anti-CEA, which is an antibody that specifically binds to CEA (Carcinoembryonic Antigen), which is a cancer-specific antigen.

After the elapse of the predetermined period of time since the fluorescent substance is administered to the body of the patient, when the operator inserts the insertion section 31 of the endoscope 11 into the body cavity of the patient and guides the distal end portion thereof to a target site of the specimen S, white light and excitation light emitted from the light-source device 10 are irradiated onto the specimen S via the light guide fiber 32 and the illumination lens 33.

At this time, in the light-source device 10, the white light and the excitation light simultaneously emitted from the xenon lamp 21 are transmitted through the illumination-light filter 23 only at predetermined ratios and enter the collimator lens 22. The collimator lens 22 makes the irradiated white light and excitation light enter the light guide fiber 32 in the form of approximately collimated light.

Here, in order that the fluorescence observation apparatus of this embodiment satisfies the conditional expression (1), the illumination-light filter 23 is configured such that the transmittance of excitation light becomes higher than the transmittance of white light. Specifically, as shown in FIG. 2, for example, because the illumination-light filter 23 is configured such that the transmittance of white light in a wavelength band from 400 to 700 nm is 30%, 30% of the white light emitted from the xenon lamp 21 and all the excitation light emitted from the xenon lamp 21 enter the collimator lens 22.

Therefore, 30% of the white light emitted from the xenon lamp 21 and all the excitation light emitted from the xenon lamp 21 are converted into approximately collimated light by the collimator lens 22, are guided by the light guide fiber 32, and are irradiated onto the specimen S via the illumination lens.

Return light that is reflected light at the specimen S upon receiving 30% of the white light emitted from the xenon lamp 21 and fluorescence that is produced when the fluorescent dye accumulated at the specimen S is excited by all the excitation light emitted from the xenon lamp 21 simultaneously enter the objective lens 34.

Those types of light are separated into the return light and the fluorescence by the beam splitter 35 and are imaged by the white-light-image acquisition unit 36 and the fluorescence-image acquisition unit 37, respectively.

A signal for a white-light image and a signal for a fluorescence image that are imaged and acquired by the white-light-image acquisition unit 36 and the fluorescence-image acquisition unit 37 are respectively output to the white-light-image generating unit 41 and the fluorescence-image generating unit 42, wherein the white-light image and the fluorescence image are generated, respectively. The white-light image and the fluorescence image are combined at the composite-image generating unit and displayed on the monitor 13.

In this way, because the illumination-light filter satisfies the conditional expression (1), with a simple configuration, it is possible to suppress paling of the fluorescent dye, to prevent saturation of the signal in the white-light image, and to ensure a sufficient amount of fluorescence.

Specifically, because the balance of white light and excitation light emitted from the light-source device 10 is maintained constant according to the conditional expression (1), it is possible to suppress saturation of the signal in the white-light image, to widen the dynamic range for observation of the white-light image, and to emit excitation light for allowing a sufficient amount of fluorescence to be produced. In other words, the sensitivity of detection of fluorescence can be ensured while ensuring a suitable dynamic range for observation of the white-light image.

Second Embodiment

A fluorescence observation apparatus according to a second embodiment of the present invention will be described below with reference to the drawings.

Figure 3:
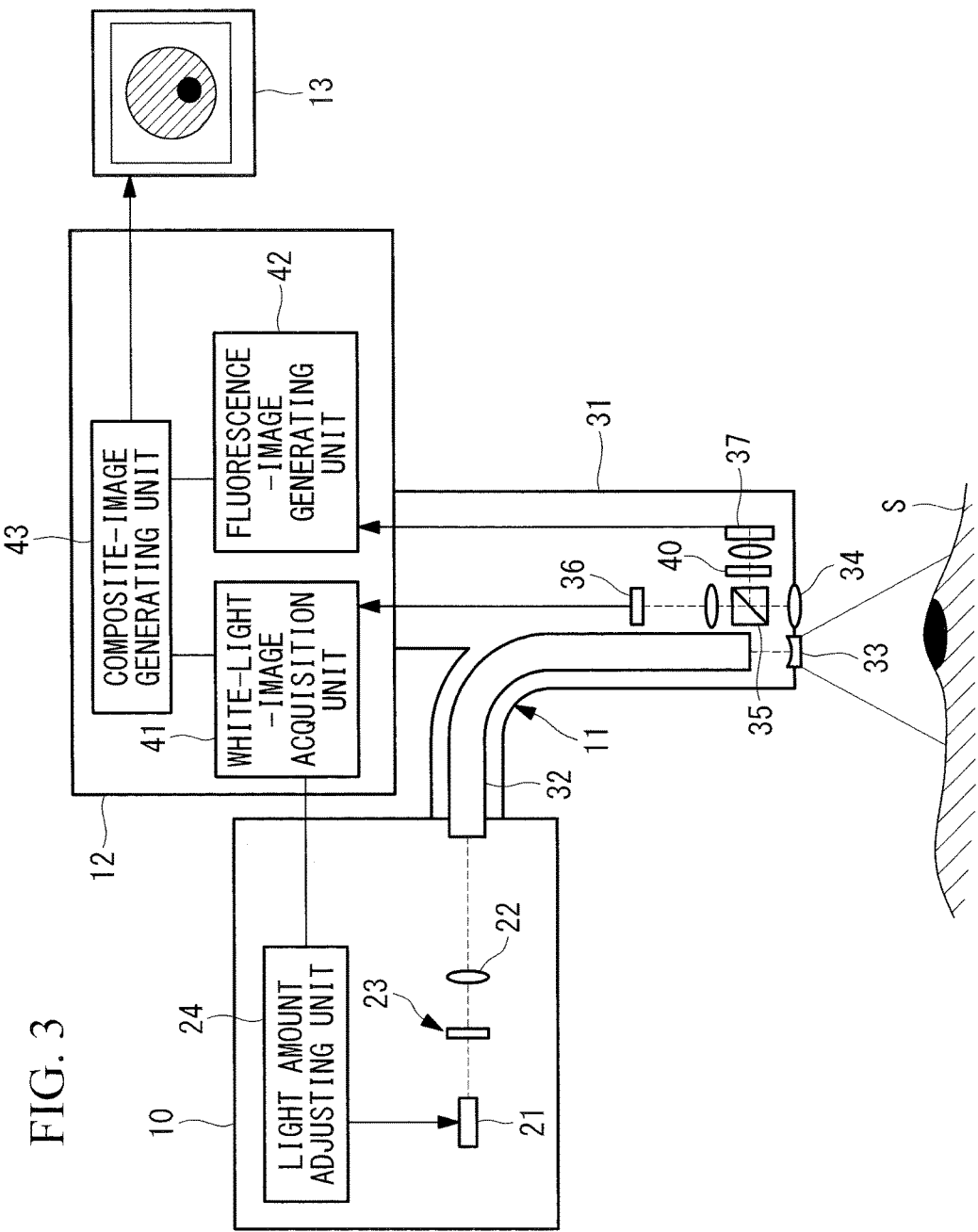
FIG. 3 is a block diagram showing, in outline, a configuration of a fluorescence observation apparatus according to a second embodiment of the present invention.

As shown in FIG. 3, the present embodiment is different from the first embodiment regarding the configuration of the light-source device in which the light-source device 10 of the fluorescence observation apparatus described above in the first embodiment further has a light amount adjusting unit 24.

The configurations which are the same as or similar to those of the fluorescence observation apparatus described in the first embodiment are accompanied with the same reference symbols, and the descriptions for those configurations are omitted.

The light-source device 10 has the light amount adjusting unit 24 which controls the xenon lamp 21 in real time so as to reduce the light intensities of the white light and the excitation light emitted from the light-source apparatus 10 as the brightness of the white-light image increases and during the observation, in response to the brightness of the white-light image acquired by the white-light-image acquisition unit 36 (for example, an average value of the gradation value). Specifically, an average gradation value of the white-light image generated by the white-light-image generating unit 41 is sent to the light amount adjusting unit 24. Next, in the light amount adjustment unit 24, a signal for controlling the amount of light based on the gradation value of the white-light image is calculated, and then is sent to a xenon lamp 21. Therefore, the light amount adjusting unit 24 is controlled based on the brightness of the white-light image so that the amount of light emitted from the xenon lamp 21 is reduced when the white-light image is too bright (for example, when the signal from of the white-light-image acquisition unit 36 is saturated), and that the amount of light emitted from the xenon lamp 21 is increased when the white-light image is too dark (for example, when the signal of the white-light-image acquisition unit 36 becomes close to a background noise level of the white-light-image acquisition unit 36).

For example, when the illumination light has a wavelength band from 400 to 800 nm and has a uniform spectrum, in order to avoid a situation in which the white-light image is to bright, a light amount control is conducted to reduce the amount of light emitted from the xenon lamp 24. By this operation, the amount of light n a wavelength band from 700 to 800 nm, which is the excitation light, is also suppressed, and therefore there is a possibility in which the brightness of fluorescence becomes insufficient.

On the other hand, when the illumination-light filter 23, whose transmittance in the wavelength band from 400 to 700 nm is suppressed, is employed, the degree of reducing the amount of light emitted from the xenon lamp is reduced because the situation, in which the brightness of the white-light image becomes too much, is prevented unless the distance between the distal end of the insertion section 31 and the specimen S becomes excessively short (for example, 1 cm). Therefore, it is possible to observe fluorescence with sufficient brightness without largely suppressing the amount of excitation light.

Also, it is expected that the white-light image becomes too bright in a particular situation in which, for example, the distal end of the insertion section 31 becomes close to the specimen S, the amount of light is automatically controlled and thereby reduced in such a situation (FIG. 3). Note that the controlled range is still small in the situation, and it is also possible to avoid a situation in which the amount of fluorescence is largely reduced because the excitation-light band from 700 to 800 nm is sufficiently bright.

The operation of the thus-configured fluorescence observation apparatus will be described below.

In the case in which, for example, the distance between the distal end of the insertion section 31 and the specimen S becomes small during the observation using the fluorescence observation apparatus of the present embodiment, the amounts of irradiated white light and excitation light on the specimen S becomes large. In this case, since the brightness of the white-light image is increased, the light amount adjusting unit 24 controls the amounts of white light and excitation light emitted from the xenon lamp 21 to reduce them, in response to the increase of the brightness of the white-light image. Therefore, it is possible to prevent the signal of the white-light-image acquisition unit 36 from being saturated, and the dynamic range for observation of the white-light image is further widened relative to the first embodiment.

A signal of the white-light image and a signal of the fluorescence image, which are formed and acquired by the white-light-image acquisition unit 36 and the fluorescence image acquisition unit 37, are respectively output to the white-light-image generating unit 41 and the fluorescence-image generating unit 42, and the white-light image and the fluorescence image are generated, respectively. The white-light image and the fluorescence image are combined at the composite-image generating unit and displayed on the monitor 13.

Figure 4A:
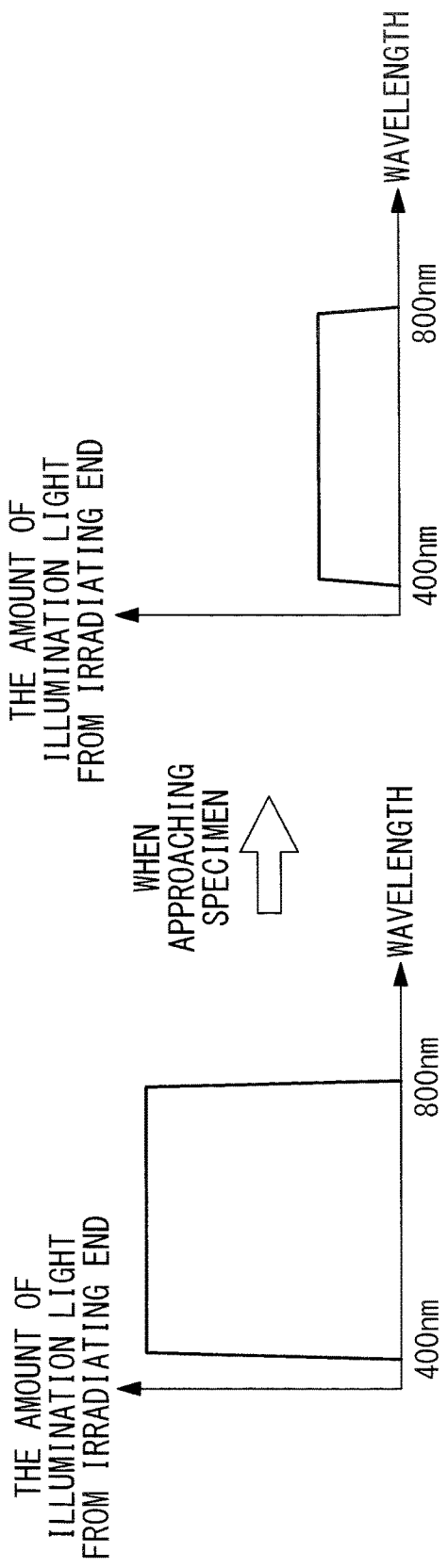
FIG. 4A is a graph showing an example of conventional light-amount adjustment control.

The transmittance spectrum of the fluorescence filter 40 does not satisfy the conditional expression (1), for example, in a case in which $Pf(\lambda w)=Pf(\lambda e)$, when the amount of irradiated light is suppressed by the light amount adjusting unit 24, the amount of the excitation light is also suppressed as well as that of the white light. For example, because the transmittance of the filter for irradiation light and excitation light is conventionally uniform, the amount of the excitation light is suppressed when the amount of the irradiation light is suppressed. (See FIG. 4A.)

This is because when said transmittance is uniform, the white-light image becomes too bright even in a situation in which the distance between the distal end of the insertion section 31 and the specimen S is not extremely small, and the amount of light is suppressed by the light amount adjusting unit 24, because intensity of reflected light of the white light is 100 or more times larger than that of the excitation light in general.

However, in this embodiment, the amount of light is adjusted in response to the brightness change of the white-light image during the observation. Thus, the balance between the white light and the excitation light emitted from the light-source device 10 is kept at a predetermined ratio (FIG. 4B). Therefore, it is possible to suppress the saturation of the signal of the white-light image unless the distance between the distal end of the insertion section 31 and the specimen S becomes extremely shot, the dynamic range for observation of the white-light image is widened, and the reduction of the excitation light is reduced relative to the case in which $Pf(\lambda w)=Pf(\lambda e)$. Therefore, it is possible to emit excitation light for allowing a sufficient amount of fluorescence to be produced.

In other words, the sensitivity of detection of fluorescence can be ensured while ensuring a suitable dynamic range for the observation. Therefore, it is possible to suppress paling of the fluorescent dye due to an excess amount of irradiated light, to prevent saturation of the signal in the white-light image, and to ensure a sufficient amount of fluorescence, while making the configuration of the fluorescence observation apparatus simple.

The light amount adjusting can be performed by controlling the xenon lamp 21 itself, and also by providing an aperture stop in the light pass.

Further, when a filter is provided in the endoscopes, it is not necessary to perform filter change for each of the endoscopes, and the optimum filter can be used in each of the endoscopes.

Modified Example

In the fluorescence observation apparatuses in the aforementioned embodiments, it is possible to configure the illumination-light filter 23 and the beam splitter 35 to satisfy the following conditional expressions.

$$Pf(\lambda w) \times Ps(\lambda w) < Pf(\lambda e) \times (1 - Ps(\lambda f)) \quad (2)$$

$$0 < Ps(\lambda) < 1$$

In the expression, $\lambda w$ is a wavelength in the white-light band, $\lambda e$ is a wavelength in the excitation-light band, $\lambda f$ is a wavelength in a fluorescence band, $Ps(\lambda)$ is a ratio with which light having a wavelength $\lambda$ is separated by the beam splitter 35 to a light path toward the white-light-image acquisition unit, and $1-Ps(\lambda)$ is a ratio with which the light at the wavelength $\lambda$ is separated by the beam splitter 35 to a light path toward the fluorescence-image acquisition unit.

By the configuration which fulfills the conditional expression (2), it is possible to appropriately maintain the relationship between the transmittance of the illumination-light filter and the ratio of dividing light at the beam splitter. Therefore, it becomes possible to prevent the saturation of the signal of the white-light image, and to enable a sufficient amount of fluorescence, while reducing the manufacturing costs of the illumination-light filter.

Figure 5:
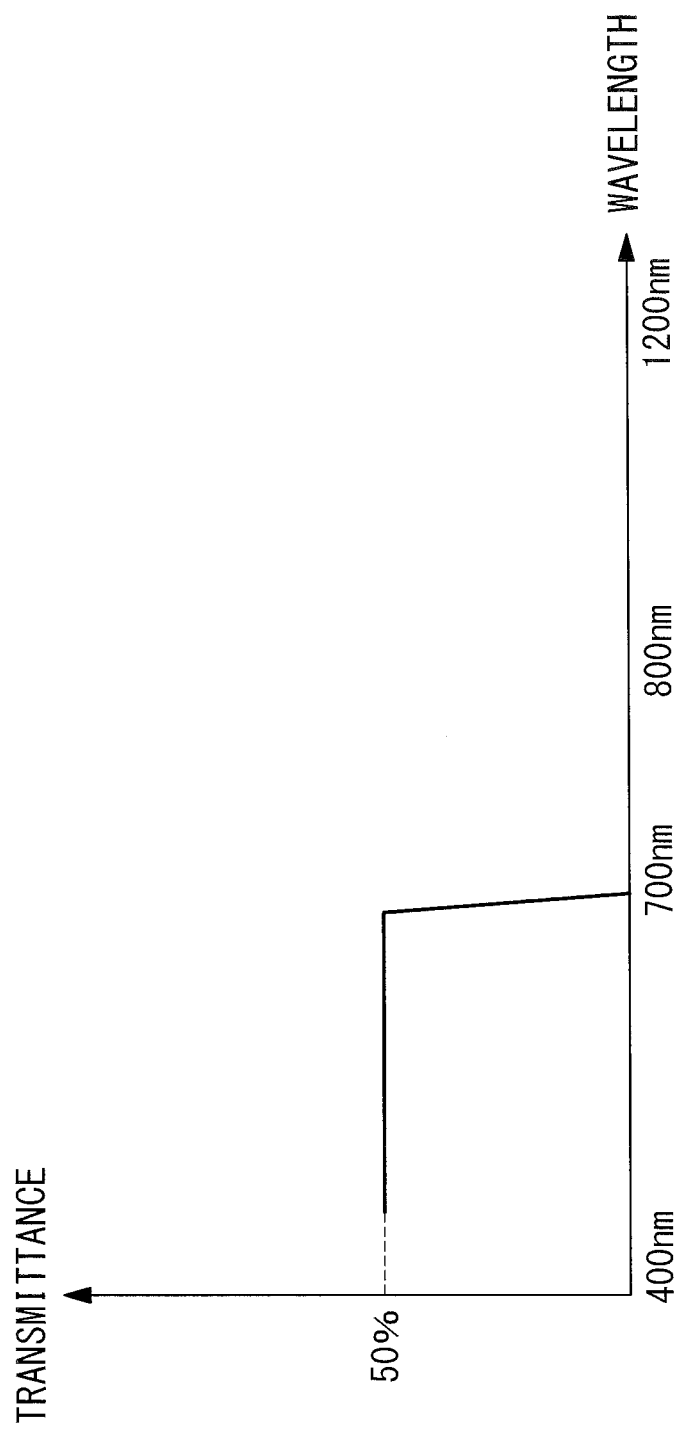
FIG. 5 is a graph showing light splitting ratios at a beam splitter applied to a fluorescence observation apparatus according to a modified example of the second embodiment of the present invention.
Figure 6:
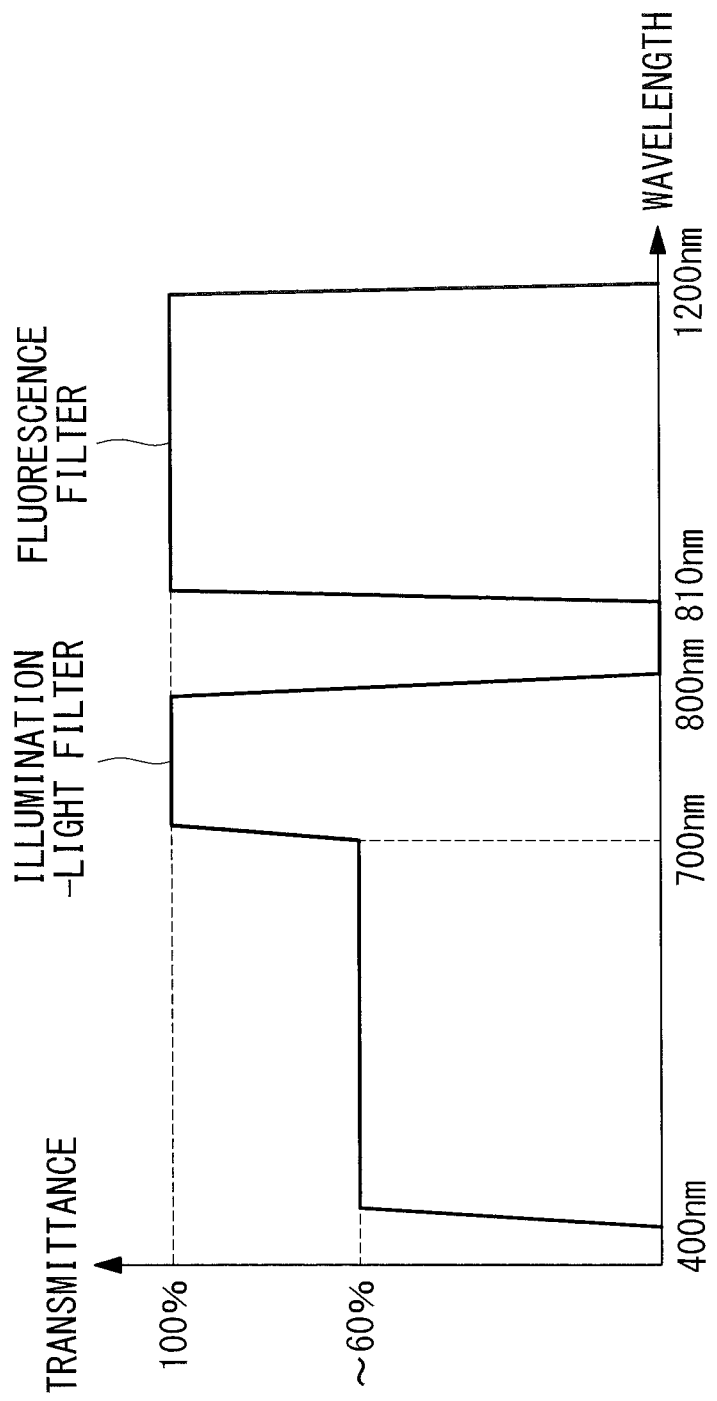
FIG. 6 is a graph showing transmittances of an illumination-light filter and a fluorescence filter applied to the fluorescence observation apparatus according to the modified example of the second embodiment of the present invention.

In other words, in addition to the fact that the transmittance of the white-light band is lower than that of the excitation-light band, when the difference is relatively small, the transmittance of the white-light band at the beam splitter is set to be 50% (FIG. 5), for example. By this, for example, when the transmittance of the white light at the illumination-light filter 23 is 60%, the return light generated by the aforementioned light is reduced by 50% at the beam splitter. Therefore, the intensity of the white light is substantially reduced to 30% by the light-source device 10.

With the aforementioned configuration, the balance between the intensity of the return light irradiated onto the white-light-image acquisition unit and the intensity of the fluorescence light irradiated onto the fluorescence-image acquisition unit becomes a level which is the same as or similar to the fluorescence observation apparatus described in the first embodiment.

Therefore, as well as the fluorescence observation apparatus described above in the first embodiment, it is possible to suppress paling of the fluorescent dye due to an excess amount of irradiated light, to prevent saturation of the signal in the white-light image, and to ensure a sufficient amount of fluorescence, while making the configuration of the fluorescence observation apparatus simple.

IN General, filters, such as the illumination-light filter, used in the light-source device are made by forming a dielectric multilayer film. Generally, in those filters, the filter which makes a relatively small transmittance difference, 100%-60%, between the wavelengths uses a smaller number of layers for production of the dielectric multilayer film than the filter which makes a large transmittance difference, 100%-30%, between the wavelength bands, which makes the design and the production easier. Therefore, by configuring the fluorescence observation apparatus to satisfy the conditional expression (2), it becomes possible to apply an illumination-light filter made of a dielectric multilayer film with a small number of layers, and thereby it becomes possible to reduce the costs for the design and the production.

Third Embodiment

A third embodiment of the present invention will be described below.

The present embodiment is different from the first embodiment describe above in the following points. The configurations which are the same as or similar to those of the fluorescence observation apparatus described in the first embodiment are accompanied with the same reference symbols, and the descriptions for those configurations are omitted.

Figure 7:
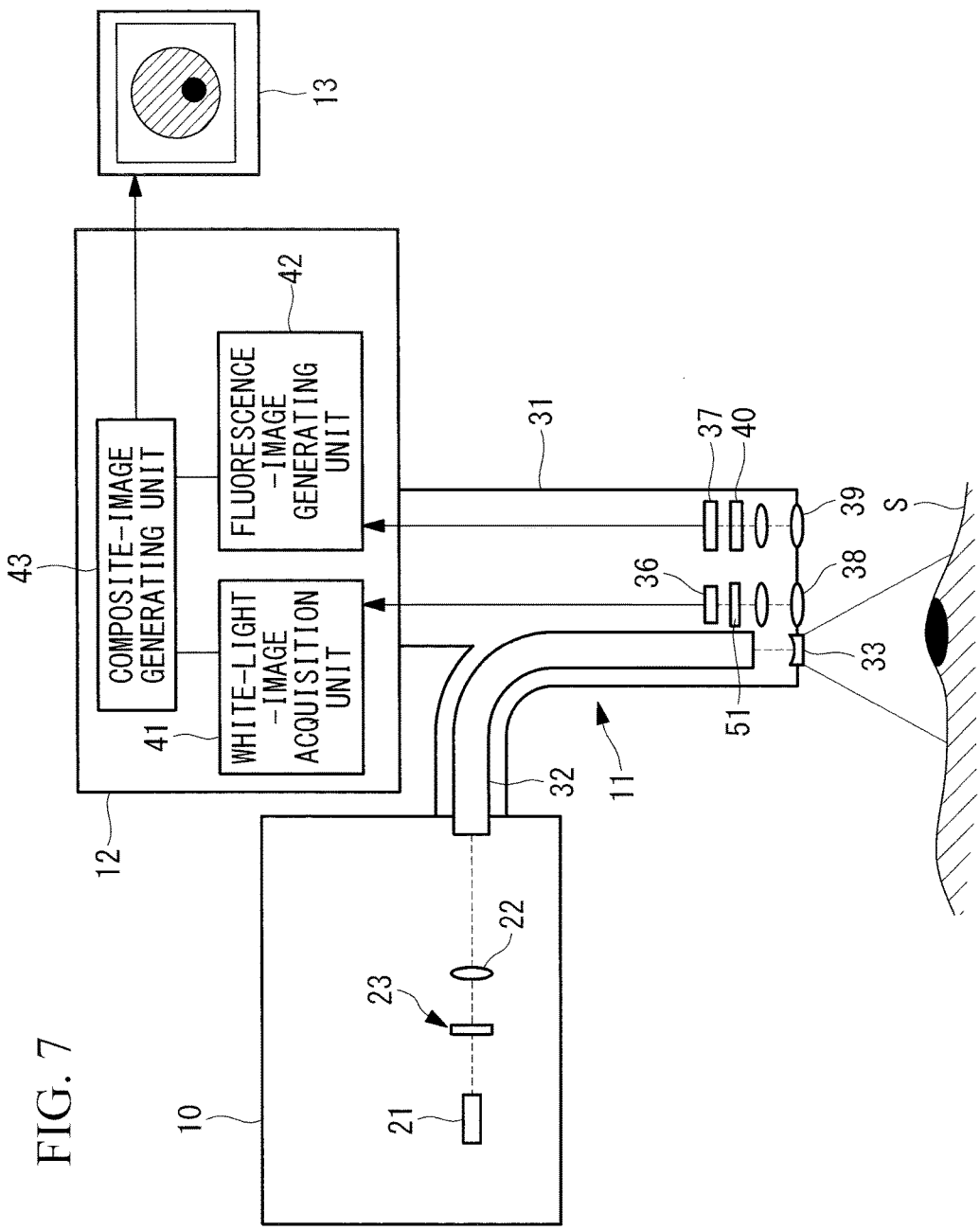
FIG. 7 is a block diagram showing, in outline, the configuration of a fluorescence observation apparatus according to a third embodiment of the present invention.

Specifically, as shown in FIG. 7, the present embodiment does not have a beam splitter, but has two objective lenses 38, 39 as an objective lens for the fluorescence observation and an objective lens for the white-light observation. Also, the white-light-image acquisition unit 36 and the fluorescence-image acquisition unit 37 are provided in the light passes of the two objective lenses 38, 39, respectively. The fluorescence filter 40 is located at a light inlet end side of the fluorescence-image acquisition unit 37, which allows light of a predetermined wavelength to go through. An attenuation filter 51 as a light attenuating part is provided between the white-light-image acquisition unit 36 and the objective lens 38.

In the fluorescence observation apparatus configured in the aforementioned way, even in a case in which the transmittance of the white-light band is lower than that of the excitation-light band, the difference between the transmittances is relatively small, and the transmittance of the white light by the illumination-light filter 23 is 60%, it becomes possible to substantially reduce the intensity of the return light to 30% by setting the transmittance of the attenuation filter 51 at 50%.

Therefore, as well as the fluorescence observation apparatus described above in the first embodiment and its modified example, it is possible to suppress paling of the fluorescent dye due to an excess amount of irradiated light, to prevent saturation of the signal in the white-light image, and to ensure a sufficient amount of fluorescence, while making the configuration of the fluorescence observation apparatus simple.

Also, it becomes possible to apply an illumination-light filter made of a dielectric multilayer film with a small number of layers, and thereby it becomes possible to reduce the costs for the design and the production.

In each of the aforementioned embodiments, it is preferable that the characteristic of the illumination-light filter is appropriately changed in accordance with the fluorescence substance used in the embodiment. In other words, it is preferable that the illumination-light filter is made so as to satisfy the following conditional expression.

$$Pf(\lambda w') < Pf(\lambda we) < Pf(\lambda e') \quad (3)$$

In the expression, λw' is a wavelength band which belongs to the white-light band and does not belong to the excitation-light band, λwe is a wavelength band which belongs to the white-light band and also the excitation-light band, and λe' is a wavelength band which belongs to the excitation-light band and does not belong to the white-light band.

For example, in the case in which Cy7 (produced by Ge Healthcare) as the fluorescence substance is employed as an alternative of ICG, the following configuration is preferable.

In the case in which AntiCEA-Cy7 is employed, the wavelength band of the fluorescence light which excites the dye is 650 to 740 nm, and part of that overlaps with the white light. In this case, it is possible to make the characteristic of the filter so that 400 to 650 nm is 30% and 650 to 740 nm is 100%. However, 650 to 700 nm belongs to the white-light band, and therefore there is a possibility that color deviation occurs in the white-light image.

Therefore, it is preferable that the transmittance of the excitation light is gradually increased in the wavelength of 650 to 700 nm in which the white-light band and the excitation-light band overlap (FIG. 8).

In other words, it is preferable that the amount of light should not be increased sharply relative to the wavelength in the wavelength which belongs to the white light and the excitation light, for example, it is preferable that the amount of light is increased with a predetermined gradient, proportionately or with stepwise increase. By this configuration, it becomes possible to obtain sufficient intensity of the excitation light, minimizing the change in color of the white-light image.

A voluntary combination of the aforementioned embodiments belongs to the scope of the present invention. In the embodiments, although the xenon lamp is employed as a light-emitting element, it is possible to employ an LED or the like as the light-emitting element. Also, although the light guide provided in the endoscope as a light guide means is employed, a catheter with optical fibers which can be inserted through the forceps channel of an endoscope, or microscope, and other devices may be employed.

It is preferable that the apparatus has a plurality of illumination-light filters whose transmittances are different from each other, and that a configuration in which the illumination-light filters are selectively inserted between the emitting portion of, for example, the xenon lamp and the radiation end of the white light and the excitation light by accommodating the filters in a turret or the like. By this configuration, it becomes possible to deal with the diversity of the fluorescence substances which would be employed.

The inventor has arrived at the following aspects of the invention.

An aspect of the present invention provides a fluorescence observation apparatus comprising: a light source unit that has a single light-emitting portion for emitting white light and excitation light simultaneously and that radiates the white light and the excitation light emitted from the light-emitting portion; a light guide part that guides the white light and the excitation light radiated from the light source unit and that simultaneously irradiates the white light and the excitation light onto a specimen; a white-light-image acquisition unit that receives return light of the white light coming from the specimen and that acquires a white-light image; and a fluorescence-image acquisition unit that receives fluorescence excited in the specimen by the excitation light and that acquires a fluorescence image, wherein the light source unit has an illumination-light filter that is disposed between the light-emitting portion and the light guide part, and that satisfies the following conditional expression, $$Pf(\lambda w) < Pf(\lambda e) \quad (1)$$

wherein Pf(λw) is a light transmittance of the illumination-light filter at a wavelength λw in a white-light band, and Pf(λe) is a light transmittance of the illumination-light filter at a wavelength λe in a excitation-light band.

According to this aspect, white light and excitation light emitted from the single light-emitting portion of the light source unit are irradiated onto the specimen via the light guide part, return light of the white light coming from the specimen is received, thus acquiring a white-light image, and fluorescence excited in the specimen by the excitation light is received, thus acquiring a fluorescence image. In this case, the illumination-light filter, which is disposed in the light source unit between the light-emitting portion and the radiation exit end, from which the white light and the excitation light are radiated, satisfies the above-described conditional expression. Therefore, with a simple configuration, it is possible to suppress paling of a fluorescent dye, to prevent saturation of the signal in the white-light image, and to ensure a sufficient amount of fluorescence.

Specifically, because the balance of white light and excitation light radiated from the light source unit is maintained at a predetermined level according to the above-described conditional expression, it is possible to suppress saturation of the signal in the white-light image, to widen the dynamic range for observation of the white-light image, and to emit excitation light which allows a sufficient amount of fluorescence to be produced. In other words, the detection sensitivity of fluorescence can be ensured while ensuring a suitable dynamic range for observation of the white-light image.

In the above-described aspect, it is preferable that the apparatus further comprises a light-amount adjusting unit that controls the light-emitting portion so that the amount of the white light and the amount of the excitation light radiated from the light source unit are decreased as a brightness of the white-light image is increased and in accordance with the brightness of the white-light image.

By doing so, even in a case in which the distance between the light source unit and the specimen is shortened, the amount of light can be suppressed by the light-amount adjusting unit. Accordingly, it is possible to suppress saturation of the signal at the white-light-image acquisition unit, thus enlarging the dynamic range for observation.

In the above-described aspect, it is preferred that the apparatus further comprises a light splitting part that separates the fluorescence from the return light so as to make the return light enter the white-light-image acquisition unit and to make the fluorescence enter the fluorescence-image acquisition unit, wherein the filter and the light splitting part satisfy the following conditional expressions, $$Pf(\lambda w) \times Ps(\lambda w) < Pf(\lambda e) \times (1 - Ps(\lambda f)) \quad (2)$$

$$0 < Ps(\lambda) < 1$$

wherein $\lambda w$ is a wavelength in the white-light band, $\lambda e$ is a wavelength in the excitation-light band, $\lambda f$ is a wavelength in a fluorescence band, $Ps(\lambda)$ is a ratio with which light having a wavelength $\lambda$ is separated by the light splitting part to a light path toward the white-light-image acquisition unit, and $1 - Ps(\times)$ is a ratio with which the light at the wavelength $\lambda$ is separated by the light splitting part to a light path toward the fluorescence-image acquisition unit.

By doing so, the relationship between the light transmittance and the light splitting part can be appropriately maintained, and it is possible to prevent saturation of the signal in a white-light image and to ensure a sufficient amount of fluorescence, while reducing the costs.

In the above-described aspect, it is preferred that the apparatus further comprises a light attenuating part provided at a position between the white-light-image acquisition unit and an objective lens which receives at least the white light coming from the specimen, for attenuating the white light.

By doing so, the irradiation of excessive return light onto the white-light-image acquisition unit can be suppressed, and it is possible to prevent saturation of the signal in the white-light image and to ensure a sufficient amount of fluorescence, while reducing the costs.

In the above-described aspect, it is preferred that at least part of the excitation-light band belongs to the white-light band and the filter satisfies the following conditional expression, $$Pf(\lambda w') < Pf(\lambda we) < Pf(\lambda e') \quad (3)$$

wherein $\lambda w'$ is a wavelength band that belongs to the white-light band but does not belong to the excitation-light band, $\lambda we$ is a wavelength band that belongs to the white-light band and also belongs to the excitation-light band, and $\lambda e'$ is a wavelength band that belongs to the excitation-light band but does not belong to the white-light band.

By doing so, the amount of light having a wavelength in the white-light band and in the excitation-light band can be increased with a constant slope, without being rapidly increased, and a sufficient amount of fluorescence can be ensured while minimizing a change in hue of a white-light image.

In the above-described aspect, it is preferred that at least part of the excitation-light band of the excitation light from the light-emitting portion exceeds 700 nm.

By doing so, it is possible to include excitation light in a near-infrared band and to ensure a sufficient amount of fluorescence when a fluorescent dye having an excitation spectrum in the near-infrared band is observed.

It is preferred that the light source unit comprises a plurality of illumination-light filters having respective light transmittances, and the illumination-light filters can be selectively inserted between the light-emitting portion and the light guide part.

By doing so, it is possible to select an appropriate illumination-light filter according to the wavelength of light to be produced in the light-emitting portion and a fluorescent substance to be administered to the specimen and to ensure a sufficient amount of fluorescence while minimizing a change in hue of a white-light image.

The aforementioned aspects can achieve an advantageous effect of suppressing fading of a fluorescent dye, preventing saturation of the signal in a white-light image, and ensuring a sufficient amount of fluorescence, with a simple configuration.

REFERENCE SIGNS LIST 10 light-source device (light-source unit)
11 endoscope
12 image processing device
13 monitor
21 xenon lamp (light-emitting portion)
22 collimator lens
23 illumination-light filter
24 light amount adjusting unit (light amount adjusting means)
31 insertion section
32 light guide fiber (light guide part)
33 illumination lens
34 objective lens
35 beam splitter (light splitting part)
36 white-light-image acquisition unit
37 fluorescence-image acquisition unit
38 objective lens
39 objective lens
40 fluorescence filter 41 white-light-image generating unit (white-light-image acquisition unit)
42 fluorescence-image acquisition unit (fluorescence-image acquisition unit)
43 composite-image generating unit
41 attenuation filter (light attenuating part)

The invention claimed is:

1. A fluorescence observation apparatus comprising:
a light source configured to simultaneously radiate white light and excitation light;
an illumination-light filter configured to simultaneously transmit a part of the white light and the excitation light, wherein the illumination-light filter is configured to have light transmittance characteristics that satisfy the following conditional expression, $$Pf(\lambda w) < Pf(\lambda e)$$

wherein $Pf(\lambda w)$ is a light transmittance of the illumination-light filter at a wavelength $\lambda w$ in a white-light band, and $Pf(\lambda e)$ is a light transmittance of the illumination-light filter at a wavelength $\lambda e$ in an excitation-light band;
a light guide configured to guide the part of the white light and the excitation light transmitted by the illumination-light filter, and to simultaneously irradiate the part of the white light and the excitation light onto a specimen;
a white-light-image sensor configured to receive return light of the part of the white light, transmitted through the illumination-light filter having the light transmittance of $Pf(\lambda w)$ at the wavelength $\lambda w$ in the white light band, coming from the specimen and acquire a white-light image; and
a fluorescence-image sensor configured to receive fluorescence excited in the specimen by the part of the excitation light, transmitted through the illumination-light filter having the light transmittance of $Pf(\lambda e)$ at the wavelength $\lambda e$, and acquire a fluorescence image.

2. The fluorescence observation apparatus according to claim 1, further comprising:
a controller configured to control the light source so that the amount of the white light and the amount of the excitation light radiated from the light source are decreased as a brightness of the white-light image is increased.

3. The fluorescence observation apparatus according to claim 2, further comprising:
a light splitter configured to separate the fluorescence from the return light so as to make the return light enter the white-light-image sensor and to make the fluorescence enter the fluorescence-image sensor,
wherein the filter and the light splitter are configured to satisfy the following conditional expressions, $$Pf(\lambda w) \times Ps(\lambda w) < Pf(\lambda e) \times (1-Ps(\lambda f))$$

$$0 < Ps(\lambda) < 1$$

wherein $\lambda w$ is a wavelength in the white-light band, $\lambda e$ is a wavelength in the excitation-light band, $\lambda f$ is a wavelength in a fluorescence band, $Ps(\lambda)$ is a ratio with which light having a wavelength $\lambda$ is separated by the light splitter to a light path toward the white-light-image sensor, and $1-Ps(\lambda)$ is a ratio with which the light at the wavelength $\lambda$ is separated by the light splitter to a light path toward the fluorescence-image sensor.

4. The fluorescence observation apparatus according to claim 2, further comprising:
a light attenuating filter provided at a position between the white-light-image sensor and an objective lens which receives the return light of the part of the white light coming from the specimen, wherein the light attenuating filter is configured to attenuate the return light of the part of the white light coming from the specimen.

5. The fluorescence observation apparatus according to claim 2,
wherein at least part of the excitation-light band belongs to the white-light band, and
wherein the illumination-light filter is configured to have light transmittance characteristics that satisfy the following conditional expression, $$Pf(\lambda w') < Pf(\lambda we) < Pf(\lambda e')$$

wherein $\lambda w'$ is a wavelength band that belongs to the white-light band but does not belong to the excitation-light band, $\lambda we$ is a wavelength band that belongs to the white-light band and also belongs to the excitation-light band, and $\lambda e'$ is a wavelength band that belongs to the excitation-light band but does not belong to the white-light band.

6. The fluorescence observation apparatus according to claim 2, wherein at least part of the excitation-light band of the excitation light radiated from the light source exceeds 700 nm.

7. The fluorescence observation apparatus according to claim 2, further comprising:
a plurality of illumination-light filters having respective light transmittances,
wherein the controller is configured to control the plurality of illumination-light filters to be selectively inserted into the optical path of the white light and the excitation light radiated by the light source.

8. The fluorescence observation apparatus according to claim 1, further comprising:
a light splitter configured to separate the fluorescence from the return light so as to make the return light enter the white-light-image sensor and to make the fluorescence enter the fluorescence-image sensor,
wherein the filter and the light splitter are configured to satisfy the following conditional expressions, $$Pf(\lambda w) \times Ps(\lambda w) < Pf(\lambda e) \times (1-Ps(\lambda f))$$

$$0 < Ps(\lambda) < 1$$

wherein $\lambda w$ is a wavelength in the white-light band, $\lambda e$ is a wavelength in the excitation-light band, $\lambda f$ is a wavelength in a fluorescence band, $Ps(\lambda)$ is a ratio with which light having a wavelength $\lambda$ is separated by the light splitter to a light path toward the white-light-image sensor, and $1-Ps(\lambda)$ is a ratio with which the light at the wavelength $\lambda$ is separated by the light splitter to a light path toward the fluorescence-image sensor.

9. The fluorescence observation apparatus according to claim 1, further comprising:
a light attenuating filter provided at a position between the white-light-image sensor and an objective lens which receives the return light of the part of the white light coming from the specimen, wherein the light attenuating filter is configured to attenuate the return light of the part of the white light coming from the specimen.

10. The fluorescence observation apparatus according to claim 1,
wherein at least part of the excitation-light band belongs to the white-light band, and wherein the illumination-light filter is configured to have light transmittance characteristics that satisfy the following conditional expression, $$Pf(\lambda w') < Pf(\lambda we) < Pf(\lambda e')$$

wherein $\lambda w'$ is a wavelength band that belongs to the white-light band but does not belong to the excitation-light band, $\lambda we$ is a wavelength band that belongs to the white-light band and also belongs to the excitation-light band, and $\lambda e'$ is a wavelength band that belongs to the excitation-light band but does not belong to the white-light band.

11. The fluorescence observation apparatus according to claim 1, wherein at least part of the excitation-light band of the excitation light radiated from the light source exceeds 700 nm.

12. The fluorescence observation apparatus according to claim 1, further comprising:
   a plurality of illumination-light filters having respective light transmittances,
   wherein the illumination-light filters are configured to be selectively inserted into the optical path of the white light and the excitation light radiated by the light source.

* * * * *